United States Patent [19]

Baldwin et al.

[11] Patent Number: 4,847,289

[45] Date of Patent: Jul. 11, 1989

[54] THIOPHENE SULFONAMIDE ANTIGLAUCOMA AGENTS

[75] Inventors: John J. Baldwin, Gwynedd Valley; Charles M. Habecker, Lansdale; Samuel L. Graham, Harleysville; Wasyl Halczenko, Hatfield; George D. Hartman, Lansdale; Harvey Schwam, Lafayette Hill; Gerald S. Ponticello, Lansdale; Kenneth L. Shepard, West Point, all of Pa.

[73] Assignee: Merck & Co., Inc., Rahway, N.J.

[21] Appl. No.: 59,084

[22] Filed: Jun. 8, 1987

[51] Int. Cl.$^4$ .................... A61K 31/38; C07D 409/00; C07D 333/32

[52] U.S. Cl. .................... 514/445; 514/444; 549/59; 549/60; 549/65

[58] Field of Search .................. 549/59, 60, 63, 65; 514/444, 445

[56] References Cited

U.S. PATENT DOCUMENTS

| | | | |
|---|---|---|---|
| 4,386,098 | 5/1983 | Woltersdorf et al. | 424/270 |
| 4,416,890 | 11/1983 | Woltersdorf et al. | 424/270 |
| 4,426,388 | 1/1984 | Woltersdorf | 424/270 |
| 4,477,466 | 10/1984 | Shepard | 424/275 |
| 4,486,444 | 12/1984 | Shepard | 424/275 |
| 4,542,152 | 9/1985 | Shepard | 514/445 |
| 4,585,787 | 4/1986 | Shepard | 514/445 |
| 4,665,090 | 5/1987 | Graham | 514/445 |
| 4,668,697 | 5/1987 | Shepard et al. | 514/443 |
| 4,677,115 | 6/1987 | Baldwin et al. | 514/432 |

FOREIGN PATENT DOCUMENTS

| | | |
|---|---|---|
| 42731 | 12/1981 | European Pat. Off. |
| 1459571 | 12/1976 | United Kingdom |

OTHER PUBLICATIONS

J. Med. Chem., 1981, 24, 959–964, Barnish et al.

*Primary Examiner*—Alan Siegel
*Attorney, Agent, or Firm*—William H. Nicholson; Michael C. Sudol, Jr.

[57] ABSTRACT

Aryl (or aralkyl)-sulfonylthiophene-2-sulfonamides containing a basic functional group as a substituent are efficacious in the treatment of elevated intraocular pressure and glaucoma following topical ocular administration.

11 Claims, No Drawings

THIOPHENE SULFONAMIDE ANTIGLAUCOMA AGENTS

SUMMARY OF THE INVENTION

This invention is concerned with novel compounds of structural formula:

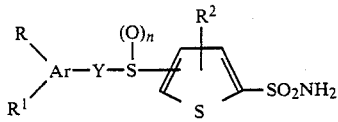

wherein R, $R^1$, $R^2$, Ar, n and Y are as defined hereinafter. These compounds are useful in the treatment of elevated intraocular pressure and glaucoma.

The invention is also concerned with novel pharmaceutical formulations comprising one of the novel compounds as active ingredient and a method of treating elevated intraocular pressure and disease states associated therewith such as glaucoma.

The invention is further concerned with novel processes for preparing the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e. the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Some β-adrenergic blocking agents are effective in reducing intraocular pressure but many of these agents also have other characteristics, e.g. membrane stabilizing activity, that cause them to be unacceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other part is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. In addition U.S. Pat. No. 4,542,152 discloses closely related aromatic sulfonylthiophene-2-sulfonamides.

DETAILED DESCRIPTION OF THE INVENTION

The novel compounds of this invention are represented by structural formula:

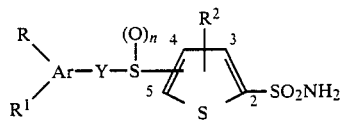

or an ophthalmologically acceptable salt thereof wherein:

Ar is an aromatic moiety selected from benzene, thiophene and furan,

R is hydrogen, hydroxy, $C_{1-3}$alkoxy, $C_{1-3}$alkyl, halo such as fluoro or chloro;

$R^1$ is hydrogen, halo such as fluoro or chloro or —X—$NR^3R^4$ wherein X is $C_{1-5}$alkylene such as

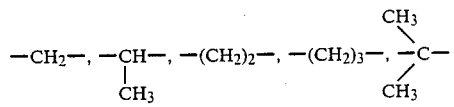

or the like;

$R^3$ is hydrogen or $C_{1-5}$alkyl; and $R^4$ is
  (a) hydrogen
  (b) $C_{1-5}$alkyl, either unsubstituted or substituted with:
    (i) hydroxy,
    (ii) $C_{1-3}$alkoxycarbonyl,
    (iii) carboxy,
    (iv) 5 or 6-membered heterocycle such as 2,3, or 4-pyridyl, furyl tetrahydrothienyl, pyrrolidinyl or the like,
    (v) $C_{3-6}$cycloalkyl or
  $R^3$ and $R^4$ if lower alkyl, may be joined together either directly or through a hetero atom to form, with the nitrogen atom to which they are attached, a 5 or 6-membered saturated heterocycle such as pyrrolidinyl, morpholinyl, piperidyl, piperazinyl, N-methylpiperazinyl, or the like.

$R^2$ is hydrogen or $C_{1-5}$alkyl, either straight or branched chain, either unsubstituted or substituted with —OH or —$NR^5R^6$ wherein $R^5$ and $R^6$ are independently selected from hydrogen, $C_{1-5}$alkyl either straight or branched chain or $R^5$ and $R^6$ if lower alkyl can be joined together to form a 5 or 6-membered heterocycle with the nitrogen to which they are attached such as piperidino, morpholino, or piperazino;

Y is
  (a) a bond,
  (b) X, or
  (c) X—$NR^5R^6$; and n is 0, 1 or 2;
with the provisos that at least one of $R^1$, $R^2$ or Y includes a basic substituent $-NR^3R^4$ or $-NR^5R^6$; and that the 3-position of the thiophene is unsubstituted.

In a preferred embodiment of the novel compounds, Ar is phenyl. It is also preferred that $R^2$ be hydrogen, or $C_{1-5}$alkyl.

A preferred sub-genus has structural formula:

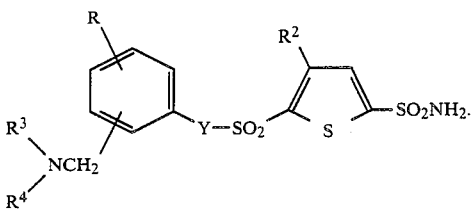

An even more preferred sub-genus has structural formula:

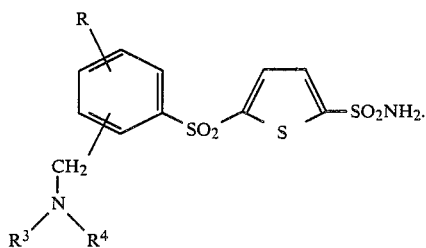

The ophthalmologically acceptable salts of the compounds of this invention include those formed from inorganic acids such as hydrochloric, sulfuric and phosphoric acids and those formed from organic acids such as maleic acid, 2-naphthalenesulfonic acid, 3,4-di-tert-butylsalicyclic acid, 2-chloro-4,6-disulfamoylphenol, 2,5-dihydroxybenzoic acid (gentisic acid), citric acid, pamoic acid, pyruvic acid, isethionic acid, fumaric acid or the like.

The novel pharmaceutical formulations of this invention are adapted for oral administration such as tablets, capsules or the like; for nasal administration, especially in the form of a spray; for injection, in the form of a sterile injectable liquid; or for topical ocular administration in the form of solutions, suspensions, ointments, gels or solid water soluble polymeric inserts.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a $\beta$-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure and glaucoma by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

The utility of the novel compounds was determined from the observation that the intraocular pressure (IOP) of the $\alpha$-chymotrypsinized rabbit eye was significantly lowered by the bilateral instillation of solutions of a representative number of the compounds shown in the following table:

EFFECT OF TOPICALLY ADMINISTERED DRUG
ON THE a-CHYMOTRYPSIN-INDUCED ELEVATION
OF IOP IN THE RABBIT (a)

| TEST COMPOUND | DOSE (%)(b) | MAX. IOPW (mm Hg)(c) |
| --- | --- | --- |
| 5-CH₃, HO, NCH₂, CH₃ structure | 0.1 | −7.0 |
| 5-isopropyl, NCH₂ structure | 0.1 | −3.7 |
| 5-H₂NCH₂ structure | 0.5 | −4.7 |

-continued
EFFECT OF TOPICALLY ADMINISTERED DRUG ON THE a-CHYMOTRYPSIN-INDUCED ELEVATION OF IOP IN THE RABBIT (a)

$$\underset{R^3R^4NX}{\overset{R}{\diagdown}}Ar-SO_2-\underset{S}{\overbrace{\phantom{XX}}}-SO_2NH_2$$

| TEST COMPOUND | DOSE (%)(b) | MAX. IOPW (mm Hg)(c) |
|---|---|---|
| 5-[morpholino-NCH2-C6H4-SO2-] | 0.1 | −4.5 |
| 4-[iBu-HNCH2-C6H4-SO2-] | 0.5 | −5.3 |
| 5-[iBu-HNCH2-furan-SO2-] | 0.5 | −4.3 |
| 5- CH3HN(CH2)3-C6H4-SO2- | 0.1 | −4.6 |
| 5-[iBu-HNCH2-thiophene-SO2-] | 0.1 | −4.7 |
| 5-[HO, N(CH3)2 substituted phenyl-(CH2)3-SO2] | 0.5 | −7.3 |

(a) Rabbits were pretreated with α-chymotrypsin at least 1 month previously in right eye only. Compound or vehicle (0.5% HEC) was instilled (50 μl) into both eyes. For full protocol see Sugrue et al, J. Pharm. Exp. Ther., 232, 534 (1985).
(b) A single 50 μl drop of the test compound was applied topically as a formulation of the indicated % concentration in freshly prepared 0.5% hydroxyethylcellulose (HEC) vehicle.
(c) The reported number is the maximum, statistically significant drop in IOP recorded during the 5 hour duration of the assay.

Another aspect of this invention is the novel processes used for preparation of the novel compounds.

For the compounds wherein the basic functional group is a free aminoalkyl, the proces comprises reduction of the corresponding nitrile, for example as shown below:

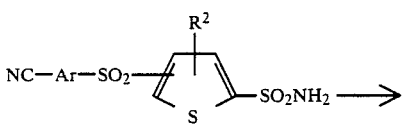

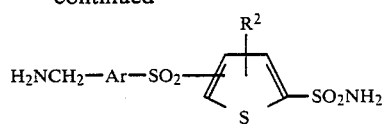

The reduction can be effected with a complex metal hydride such as $NaBH_3$ ($OCOCF_3$) in an ethereal solvent such as diethyl ether, THF, 1,2-dimethoxyethane or the like at about −10° to +30° C. for about 1 to 4 hours. Excess hydride is quenched with dilute acid.

Other reducing agents useful in this process include lithium triethylborohydride and sodium bis-(2-methoxyethoxy)aluminum hydride.

One process for preparing substituted amino compounds of the invention is a sequential Schiff base formation and reduction which can be exemplified as follows:

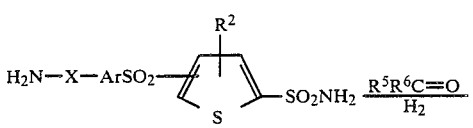

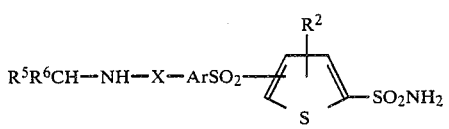

wherein R⁵R⁶CH— is R⁴.

The ketone or aldehyde, identified above as R⁵R⁶C=O, and the amine in a lower alkanol solvent such as ethanol are treated with an hydrogenation catalyst such as platinum oxide or palladium on carbon and agitated in a hydrogen atmosphere of about 15 to 65 psi, (22.3 to 96 Nm⁻²) for about 1 to 4 hours.

The reduction may also be accomplished with NaBH₃CN in an ethereal solvent.

Another process for preparing substituted amino compounds is the reduction of an amide:

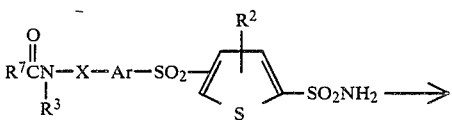

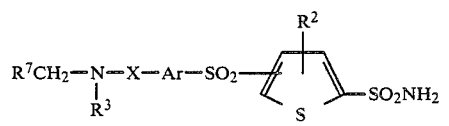

wherein R⁷CH₂— is R⁴.

Similarly novel amino compounds of this invention also may be prepared by reduction of the amide, shown below:

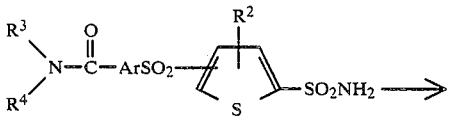

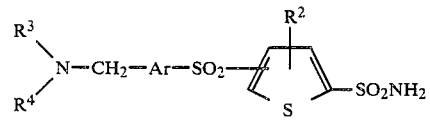

The reduction comprises treating a solution of the amide in an ethereal solvent such as diethyl ether, THF or 1,2-dimethoxyethane slowly with borane-methyl sulfide complex at about 5° to 60° C. for about 1 to 24 hours.

The dimethylamino compounds of this invention are conveniently prepared by an Eschweiler-Clarke reaction exemplified as follows:

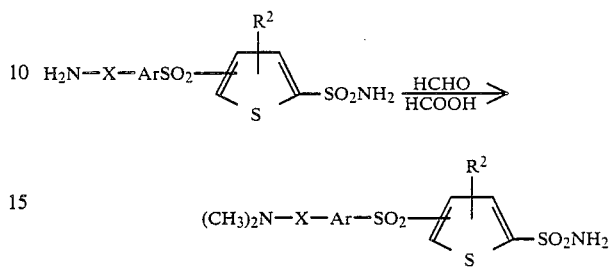

A mixture of the amino compound, formic acid and formaldehyde are heated at about steam bath temperature for about 8 to 24 hours.

For those novel compounds wherein Ar is phenyl and R is —OH, the amino compounds are readily prepared by a Mannich reaction as represented by:

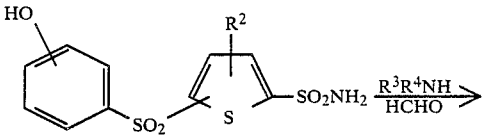

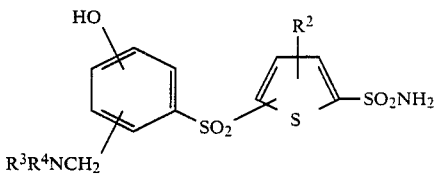

The reaction comprises refluxing a mixture of the phenol, aqueous secondary amine and formalin in ethanol for about 12 to 36 hours.

Another process suitable for making some of the novel compounds is alkylation of the amine of formula R³R⁴NH:

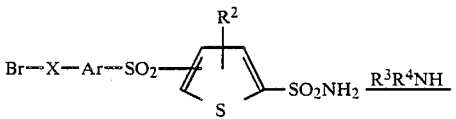

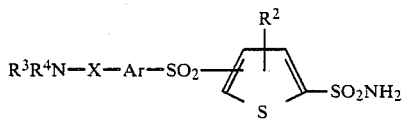

The reaction comprises mixing the two reagents in an ethereal solvent such as diethyl ether, THF, 1,2-dimethoxyethane or the like at about 10° to 30° C. for about 8 to 24 hours.

Some of the novel compounds may also be made by alkylation of the anion formed by treatment of an aromatic sulfonyl compound with n-butyllithium with an imminium salt exemplified as follows:

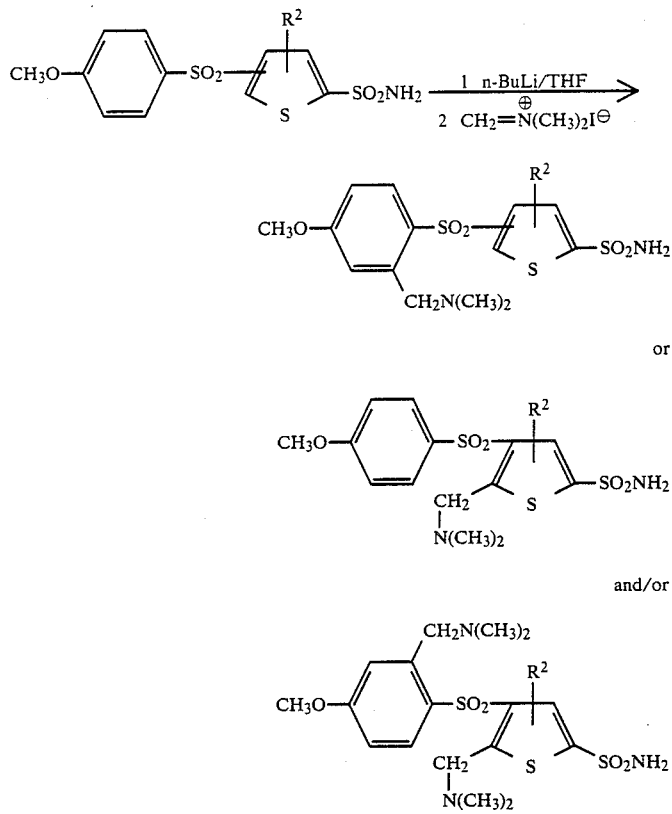

An additional process for preparing the novel compounds may be illustrated as follows:

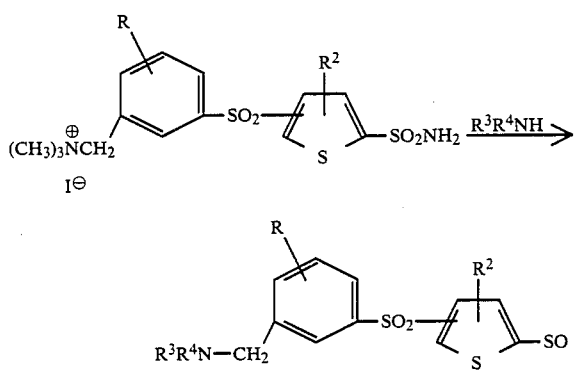

The quaternary iodide and the amine are heated together at about 50°-80° C. for about 1 to 4 hours.

This invention is also concerned with novel intermediates in the synthesis of the pharmacologically active compounds of this invention. These intermediates are represented by structural formula:

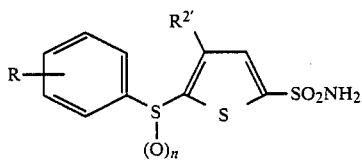

wherein n and R are as previously defined and $R^2$ is $C_{1-5}$ hydroxy alkyl.

Preferred embodiments of this class are those wherein $R^2$ is 1-hydroxyethyl, R is hydroxy or methoxy and n is 0 or 2.

EXAMPLE 1

5-[4-Aminoethyl-2-fluorophenylsulfonyl]thiophene-2-sulfonamide

Step A: Preparation of (4-cyano-2-fluorophenylthio)thiophene

Sodium hydride (1.80 g 60% dispersion in oil, 0.045 mol) was washed with petroleum ether then suspended in freshly degassed DMF (50 ml). Thiophene thiol (5.22 g, 0.045 mol) was added dropwise under nitrogen and the mixture was stirred until gas evolution ceased. 3,4-Difluorobenzonitrile (5.0 g, 0.036 mol) was added portionwise and the mixture was refluxed about 1.5 hours, after which the mixture was cooled to room temperature. The reaction mixture was poured into cold $H_2O$ and extracted with 3×100 ml ether. The ether extracts were washed with water and brine, then treated with decolorizing carbon and magnesium sulfate. After filtration and evaporation of the solvent the residual (8.46 g) oil crystallized.

Step B: Preparation of 5-[4-cyano-2-fluorophenylthio]thiophene-2-sulfonic acid potassium salt Acetic anhydride (7.34 g, 0.072 mol) was added to (4-cyano-2-fluorophenylthio)thiophene (8.46 g, 0.036 mol) in 200 ml ethyl acetate at 0° C. A cooled solution of sulfuric acid (3.88 g, 0.0395 mol) and ethyl acetate (10 ml) was added dropwise and allowed to stir at room temperature overnight. After cooling to 0° C. potassium acetate (4.23 g, 0.043 mol) in a minimum amount of ethanol was added slowly. A white solid (11.70 g) was collected after stirring one hour.

Step C: Preparation of 5-[4-cyano-2-fluorophenylthio]thiophene-2-sulfonamide The potassium salt of 5-[4-cyano-2-fluorophenylthio]-thiophene-2-sulfonic acid (11.70 g, 33.12 mmol) was suspended in ethyl acetate and oxalyl chloride (8.41 g, 66.23 mmol) then cooled to $-50°$ C., DMF (1.21 g, 16.56 mmol) was added dropwise and stirring at room temperature was continued overnight. The mixture was then cautiously diluted with 150 ml of brine. After washing the organic layer with $H_2O$, 50 ml of concentrated $NH_4OH$ was added and the mixture was stirred for 2 hours. The solution was made acidic with HCl and diluted with water. The layers were separated and the organic phase was dried over $MgSO_4$, filtered and concentrated to dryness to give 4.83 g of solid.

Step D: Preparation of 5-[4-cyano-2-fluorophenylsulfonyl]thiophene-2-sulfonamide 5-[4-cyano-2-fluorophenylthio]thiophene-2-sulfonamide (4.83 g, 15.33 mmol) and 5 ml of 30% $H_2O_2$ were dissolved in 75 ml of acetic acid. This solution was heated on a steam bath overnight. The hot solution was then poured onto 300 g of ice and stirred one hour. Filtration gave 3.3 g of white solid, mp=200°-202° C.

Step E: Preparation of 5-[4-aminomethyl-2-fluorophenylsulfonyl]thiophene-2-sulfonamide Sodium borohydride (1.8 g, 47.55 mmol) was suspendedd in THF and cooled to 0° C. Trifluoroacetic acid (5.42 g, 47.55 mmol) was added to the cool mixture at such a rate to maintain a temperature of less than 20° C. and stirring was continued until gas evolution ceased, 5-[4-cyano-2-fluorophenylsulfonyl]thiophene-2-sulfonamide (3.3 g, 9.51 mmol) was added portionwise and the suspension was stirred for two hours. The reaction was quenched with 40 ml of 10% HCl and the THF was evaporated in vacuo. The aqueous mixture was extracted with ethyl acetate then neutralized with sodium bicarbonate. This neutral solution was extracted with $3 \times 50$ ml of ethyl acetate. After drying over $MgSO_4$ and filtering the solvent as evaporated to give 3.9 g of a solid.

Chromatography (50 mm×5 in, 230–400 mesh silica gel; chloroform/methanol 8:2) gave 2.57 g of product as a white solid. This solid was dissolved in 30 ml of methanolic HCl and concentrated to dryness to give 2.57 g of product as the hydrochloride salt, m.p. 247°–250° C. Anal Calc×d. for $C_{11}H_{11}FN_2O_4S_3 \cdot HCl$: C, 34.15; H, 3.13; N, 7.24. Found: C, 34.39; H, 3.24; N, 7.19

Following the procedure substantially as described in Example 1, Steps A through E but substituting the appropriate halonitrile for the 3,4-difluorobenzonitrile used in Step A, the 5-(aminomethylarylsulfonyl)thiophene-2-sulfonamides depicted in Table I are prepared:

TABLE I

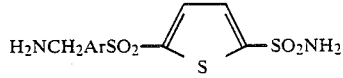

| $H_2NCH_2ArSO_2-$ | m.p.(°C) |
|---|---|
| 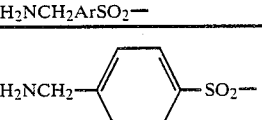 | 304–305 HCl salt) |
| 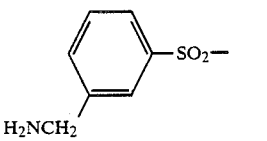 | 125–127<br>114–117 (HCl salt) |
| 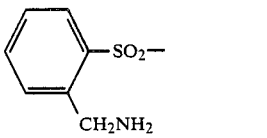 | 235–237 (HCl salt) |
| 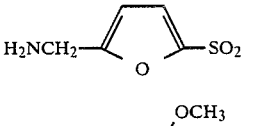 | 220–223 (HCl salt) |
| 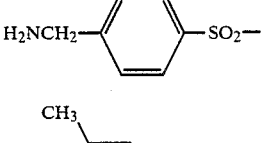 | — |
| 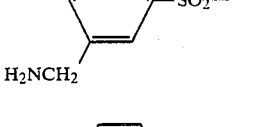 | — |
| 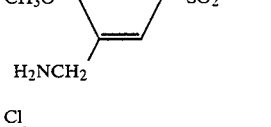 | — |
| 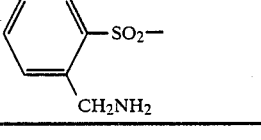 | — |

EXAMPLE 2

5-[4-n-Propylaminomethylphenylsulfonyl]thiophene-2-sulfonamide

5-[4-aminomethylphenylsulfonyl]thiophene-2-sulfonamide (1.9 g, 5.15 mmol) and propionaldehyde (0.314 g, 5.40 mmol) were dissolved in ethanol (75 ml). Platinum oxide (300 mg) was added and the mixture was hydrogenated in a Parr apparatus at about 65 psi (96 $Nm^{-2}$) for about 2 hours. The mixture was filtered through a filter aid and evaporated to dryness. The residual oil was chromatographed (50 mm×5 in, 230–400 mesh silica gel; chloroform methanol, 9 to 1 respectively) and the appropriate fractions were combined and treated with methanolic HCl. Evaporation of the solvent left a white solid which after drying for 2 hours under high vacuum at room temperature, had m.p. 151°–153° C. Anal Calc'd. for: $C_{14}H_{18}N_2O_4S_3 \cdot HCl$: C, 40.91; H, 4.65; N, 6.82. Found: C, 40.72; H, 4.60; N, 6.89.

Following the procedure substantially as described in Example 2 but substituting for the propionaldehyde and the aminoethyl starting materials used therein, the respective aldehyde of ketone and aminomethyl compound there are prepared the substituted aminomethyl compounds depicted in Table II:

TABLE II $$R^4-NH-CH_2-Ar-SO_2-\underset{S}{\text{thiophene}}-SO_2NH_2$$

| $R^4NHCH_2ArSO_2-$ | m.p. (°C.) |
|---|---|
| i-C₃H₇NHCH₂—⟨C₆H₄⟩—SO₂— | 169–172 (HCl salt) |
| i-C₄H₉NHCH₂—⟨C₆H₄⟩—SO₂— | 198–200 (HCl salt) |
| i-C₄H₉NHCH₂—⟨C₆H₃F⟩—SO₂— | 123–125 (HCl salt) |
| sec-C₄H₉NHCH₂—⟨C₆H₃F⟩—SO₂— | 193–195 (HCl salt) |
| ⟨C₆H₄⟩(SO₂—)(CH₂NH(CH₂)₅OH) | 80–83 (HCl salt) |
| ⟨C₆H₄⟩(SO₂—)(CH₂NH—C₄H₉—i) | 210 (HCL salt) |
| i-C₄H₉NHCH₂—⟨C₆H₄⟩—SO₂— | 109–112 (HCl, H₂O) |

TABLE II-continued $$R^4-NH-CH_2-Ar-SO_2-\underset{S}{\text{thiophene}}-SO_2NH_2$$

| $R^4NHCH_2ArSO_2-$ | m.p. (°C.) |
|---|---|
| C₂H₅NHCH₂—⟨C₆H₄⟩—SO₂— | 166–169 (1.25 HCl) |
| i-C₄H₉NHCH₂—⟨furan⟩—SO₂— | 166–168 (HCl salt) |
| (CH₃)₃CCH₂NHCH₂—⟨furan⟩—SO₂— | 180–182 (HCl salt) |
| (CH₃)₃CCH₂NHCH₂—⟨thiophene⟩—SO₂— | |
| i-C₄H₉NHCH₂—⟨thiophene⟩—SO₂— | |
| sec-C₄H₉NHCH₂—⟨thiophene⟩—SO₂— | |
| n-C₃H₇NHCH₂—⟨thiophene⟩—SO₂— | |
| ⟨C₆H₄⟩(SO₂—)(NHCH₂-tetrahydropyran) | |
| CH₃O₂CCHNHCH₂(CH₃)—⟨furan⟩—SO₂— | |
| C₂H₅—NHCH₂—⟨C₆H₃F⟩—SO₂— | |
| CH₃O—⟨C₆H₃⟩—SO₂— with C₂H₅HNCH₂ | |
| HC₃—⟨C₆H₃⟩—SO₂— with C₃H₇HNCH₂ | |

TABLE II-continued

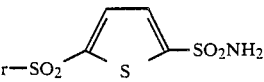

| R⁴NHCH₂ArSO₂— | m.p. (°C.) |
|---|---|

TABLE III

| R³R⁴NCH₂ArSO₂— | m.p. (°C.) |
|---|---|

EXAMPLE 3

5-[2-Fluoro-4-ethylaminomethylphenylsulfonyl]thiophene-2-sulfonamide

Step A: Preparation of 5-[2-Fluoro-4-acetylaminomethylphenylsulfonyl]thiophene-2-sulfonamide 5-[2-fluoro-4-aminoethylphenylsulfonyl]thiophene-2-sulfonamide (0.3 g, 0.86 mmol) was dissolved in 20 ml THF and cooled in an ice/acetone bath. To this solution acetic anhydride (0.087 g, 0.86 mmol) and triethylamine (0.087 g, 0.86 mmol) were added. Stirring was continued at 0° C. for 30 minutes. The mixture was filtered and solvent was evaporated to give 0.3 g of an oil. Chromatography (20 mm×5 in, 20-400 mesh silica gel, chloroform, methanol 9:1) gave 0.2 g white solid which was slurried with 10 ml 3N HCl, filtered and dried 48 hours at 60° C. under high vacuum to give product, m.p. 174°-176° C.

Step B: Preparation of 5-[2-Fluoro-4-ethylaminomethylphenylsulfonyl]thiophene-2-sulfonamide 5-[2-Fluoro-4-acetylaminomethylphenylsulfonyl]thiophene-2-sulfonamide (3.16 g, 8.05 mmol) was dissolved in THF and cooled to 10° C. Borane methyl sulfide (8.04 ml, 16.08 mmol) was added dropwise and allowed to stir overnight at room temperature. The reaction mixture was diluted with 50 ml of 6N HCl and the THF was evaporated in vacuo. The aqueous mixture remaining was filtered and allowed to cool. The white solid precipitate was collected and dried at 60° C. under high vacuum, m.p. 146°-148° C. Anal. Calc'd. for $C_{13}H_{15}FN_2O_4S_3 \cdot H_2O$, HCl: C, 36.83; H, 4.04; N, 6.61. Found: C, 36.91; H, 4.08; N, 6.81.

Following the procedure substantially as described in Example 3, but substituting the appropriate acid anhydride or acid chloride for acetic anhydride and using the appropriate aminomethyl compounds followed by reducing the resulting amide as in Step B, the compounds depicted in Table III are prepared:

EXAMPLE 4

5-[4-Dimethylaminomthylphenylsulfonyl]thiophene-2-sulfonamide

5-[4-aminomethylphenylsulfonyl]thiophene-2-sulfonamide (1.7 g, 4.6 mmol); formic acid (1.73 g, 23 mmol) and formaldehyde (0.865 g, 10.12 mmol) were combined with cooling, then refluxed on a steam bath overnight. The solvents were removed under pressure and the residue taken up in warm 10% HCl, upon cooling a white solid precipitated which was collected (0.90 g). After recrystallizing from 2-propanol, and drying at 100° C. overnight it had m.p. 225°-228° C. Anal Calc'd. for $C_{13}H_{16}N_2O_4S_3 \cdot HCl$: C, 39.33, H, 4.32; N, 7.06. Found: C, 39.59; H, 4.01; N, 7.01.

Following the procedure substantially as described in Example 4 but substituting for the starting material used therein the corresponding 3-aminomethyl compound, there was produced 5-(3-dimethylaminomethylphenylsulfonyl)thiophene-2-sulfonamide hydrochloride, m.p. 147°-150° C.

EXAMPLE 5

5-[4-(2-dimethylaminobutyl)phenylsulfonyl]thiophene-2-sulfonamide

Step A: Preparation of 5-(4-carboxymethylphenylthio)thiophene-2-sulfonamide

4-Mercaptophenylacetic acid (2.3 g) was dissolved in dimethylformamide under a nitrogen atmosphere and 1.8 g of potassium hydroxide dissolved in a minimum amount of water was added. 5-bromothiophene-2-sulfonamide (3.3 g) dissolved in dimethylformamide was added and the mixture heated at 120° C. for 2 hours. After cooling to room temperature water was added to the reaction mixture, the pH was adjusted to 8.6 and the mixture was extracted with ethyl acetate. The aqueous phase was separated and acidified, causing a solid to precipitate. The solid was collected by filtration and dried under vacuum to a weight of 3.25 g.

Step B: Preparation of 5-(4-carboxymethylphenylsulfonyl)thiophene-2-sulfonamide The solid from Step A was dissolved in methanol, and an equal volume of water was added followed by 12 g of Oxone ®. The reaction mixture was stirred at room temperature until thin layer chromatography showed no starting material remained. Solids were filtered from the reaction mixture and the filtrate was concentrated under vacuum to remove methanol. The solid-liquid residue thus obtained was filtered and the solid was washed with water and dried under vacuum to a weight of 3.2 g. This solid was shown to be a mixture of desired carboxylic acid and its methyl ester. The solid was dissolved in ethyl acetate and extracted with aqueous sodium bicarbonate. The aqueous phase was separated and acidified.

The resulting solid precipitate was collected by filtration and recrystallized from 60% ethanol-40% water, m.p. 221°–224° C. N.M.R. (acetone, $d_6$) δ: 3.80 (2H, s), 7.17 (2H, broad s), 7.60 (3H, m), 7.76 (1H, d), 8.01 (2H, d). Anal Calc'd for: $C_{12}H_{11}NO_6S_3$: C, 39.88; H, 3.07; N, 3.88. Found: C, 40.46; H, 3.23; N, 3.86.

In a similar manner 5-[4-(2-carboxyethyl)phenylsulfonyl]thiophene-2-sulfonamide (m.p. 195°–197° C.) and 5-[4-(3-carboxypropyl)phenylsulfonyl]thiophene-2-sulfonamide (m.p. 124°–126° C.) were synthesized.

Step C: Preparation of 5-(4-dimethylcarbamoylmethylphenylsulfonyl)thiophene-2-sulfonamide 5-(4-carboxymethylphenylsulfonyl)thiophene-2-sulfonamide (1.6 g) was dissolved in 50 ml of tetrahydrofuran and 0.72 g of carbonyldiimidazole was added. After stirring for one hour at room temperature excess aqueous dimethylamine was added and the mixture stirred overnight. The reaction mixture was concentrated under vacuum and the residue partitioned between ethyl acetate and water. The organic phase was separated, dried over sodium sulfate and concentrated under vacuum, giving an oil weighing 1.35 g, N.M.R. (acetone, $d_6$) δ: 2.92 (3H, s), 3.08 (3H, s), 3.84 (2H, s), 7.02 (2H, s), 7.50 (3H, m), 7.65 (1H, d), 7.90 (2H, d). The following compounds were also made by similar procedures: 5-(4-ethylcarbamoylmethylphenylsulfonyl)thiophene-2-sulfonamide, 5-[4-(2-methylcarbamoylethyl)phenylsulfonyl]thiophene-2-sulfonamide, and 5-[4-(3-dimethylcarbamoylpropyl)phenylsulfonyl]thiophene-2-sulfonamide.

Step D: Preparation of 5-[4-(2-dimethylaminobutyl)phenylsulfonyl]thiophene-2-sulfonamide 5-(4-dimethylcarbamoylmethylphenylsulfonyl)thiophene-2-sulfonamide (1.35 g) was dissolved in 30 ml of tetrahydrofuran under a nitrogen atmosphere. Borane tetrahydrofuran complex (8 ml of 1 molar solution) was added and the mixture was stirred at room temperature for 3 hours. Hydrochloric acid (20 ml of 6N) was then added cautiously and the mixture was heated on a steam bath, boiling off tetrahydrofuran. The acidic solution was cooled to room temperature and extracted with chloroform. The aqueous phase was separated and its pH adjusted to pH 8.5 before extracting it with ethyl acetate. The ethyl acetate phase was dried over sodium sulfate and concentrated under vacuum to give a residue of an oily solid. This was chromatographed on silica gel to give a pure product, m.p. 169°–172° C. N.M.R. (DMSO, $d_6$) δ: 2.17 (6H, s), 2.50 (2H, T, J=6 Hz), 2.82 (2H, T, J=6 Hz), 7.55 (2H, d, J=9 Hz), 7.60 (1H, d, J=4 Hz), 7.87 (1H, d, J=4 Hz), 7.94 (2H, d, J=9 Hz), 8.04 (2H, broad s). Anal Calc'd for $C_{14}H_{18}N_2O_4S_3$: C, 44.90; H, 4.84; N, 7.48. Found: C, 44.54; H, 4.89; N, 7.60. The following compounds where also made by similar procedures: 5-[4-(2-ethylaminoethyl)phenylsulfonyl]thiophene-2-sulfonamide (m.p. 174–177). 5-[4-(3-methylaminopropyl)phenylsulfonyl]thiophene-2-sulfonmide (m.p. 178°–179.5° C.), 5-[4-(3-dimethylaminopropyl)phenylsulfonyl]thiophene-2-sulfonamide (m.p. 163°–164.5° C.), and 5-[4-(4-dimethylaminobutyl)phenylsulfonyl]thiophene-2-sulfonamide (m.p. 186°–189° C.).

EXAMPLE 6

5-(3-Dimethylaminomethyl-4-hydroxyphenylsulfonyl)-thiophene-2-sulfonamide

A mixture of 5-(4-hydroxyphenylsulfonyl)thiophene-2-sulfonamide (15 g, 0.047 mole), 40% aqueous dimethylamine (15.7 ml, 0.14 mole), formalin solution (3.5 mL, 13.3M, 0.047 mole) in absolute ethanol (50 ml) was refluxed for eighteen hours. The solvent was removed, the residue dissolved in water and the pH adjusted to 6. The aqueous solution was extracted with ethyl acetate and the organic extract was chromatographed over silica gel using chloroform-methanol-ammonium hydroxide (90:10:1). The product, 5.8 g, was converted to its hydrochloride salt by treatment with ethanolic hydrogen chloride, m.p. 233° C.

Employing the procedure substantially as described in Example 6 but starting with the appropriate amine and hydroxyphenylsulfonylthiophene-2-sulfonamide there are prepared:

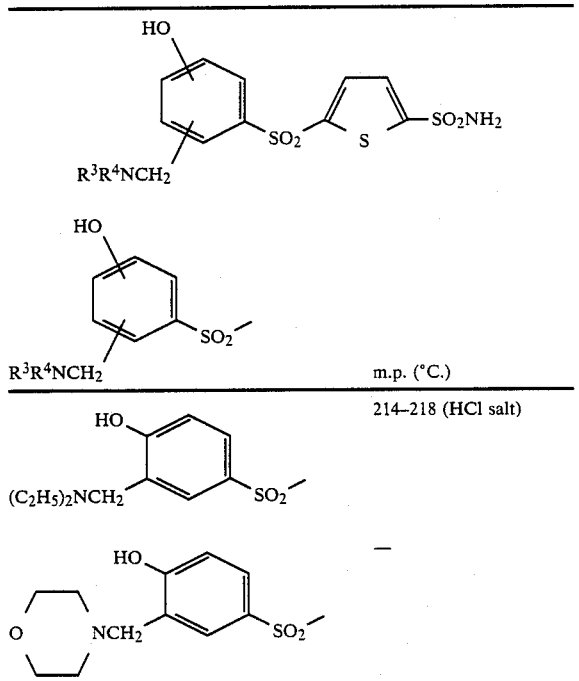

-continued

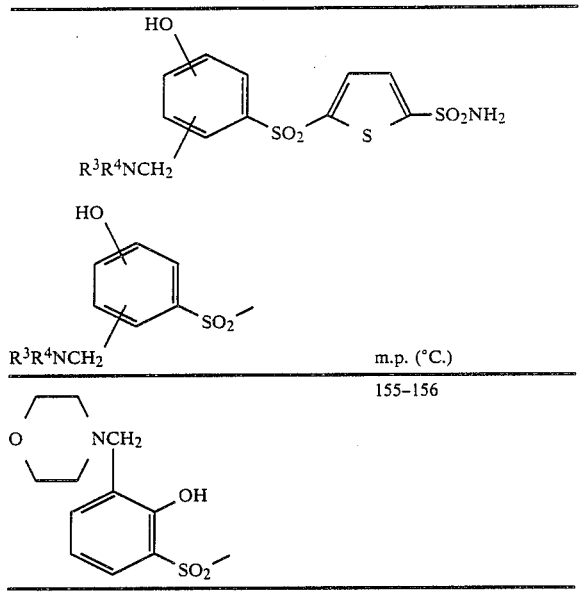

| | m.p. (°C.) |
|---|---|
| (structures) | 155-156 |

EXAMPLE 7

5-[4-Isobutylaminomethylphenylsulfonyl]thiophene-2-sulfonamide

Step A: Preparation of N,N-dimethyl-N$^1$-[5-(4-methylphenylsulfonyl)thiophene-2-sulfonyl]formamidine DMF dimethyl acetal (4.34 g, 0.036 mol) was added dropwise to a suspension of 5-[4-methylphenylsulfonyl]-thiophene-2-sulfonamide (10.5 g, 0.033 mol) in acetonitrile (100 ml). After stirring about one hour, the solvent was evaporated, the residue was slurried with alcohol and again the solvent was evaporated. After drying overnight at 60° C. under high vacuum there was obtained 12.14 g of product, m.p. 124°-126° C.

Step B: Preparation of N,N-dimethyl-N$^1$-[5-(4-bromomethylphenylsulfonyl)-thiophene-2-sulfonyl]formamidine N,N-dimethyl-N$^1$-[5-(4-methylphenylsulfonyl)thiophene-2-sulfonyl]formamidine (0.372 g, 1 mmol), N-bromosuccinimide (NBS) (0.445 g, 2.5 mmol), and a catalytic amount of benzoylperoxide were dissolved in 15 ml chloroform. This solution was refluxed and irradiated with a sun lamp for 10 minutes. Another equivalent of NBS was added and the solution was refluxed and irradiated for 30 additional minutes. The mixture was cooled and washed with 3×20 ml of H$_2$O; 1× with 1.5 g sodium thiosulfate in 30 ml H$_2$O; then dried over Na$_2$SO$_4$. Removal of the solvent left 0.4 g of a bromomethyl and dibromomethyl mixture.

Step C: Preparation of 5-[4-isobutylaminomethylphenylsulfonyl]thiophene-2-sulfonamide N,N-dimethyl-N$^1$-[5-(4-bromomethylphenylsulfonyl)thiophene-2-sulfonyl]formamidine (0.4 g, 0.89 mmol) and isobutylamine (0.065 g, 0.89 mmol) were dissolved in THF and allowed to stir at room temperature overnight. Solvent removal left an oil which was chromatographed (20 mm×5 in, 230-400 mesh silica gel, chloroform; methanol; 9:1) to give 0.08 g. The oil was then treated with 10% sodium hydroxide (5 ml) and heated on a steam bath for 1 hour. The solution was neutralized and extracted with 2×15 ml of ethyl acetate. The extracts were washed with brine, dried over MgSO$_4$, filtered and evaporated to dryness. The oily residue was dissolved in ethanolic HCl and concentrated to dryness. The solid product (0.08 g) had m.p. 198°-200° C.

EXAMPLE 8

5-(3-Dimethylaminomethyl-4-hydroxyphenylsulfonyl)-4-methylthiophene-2-sulfonamide

Step A: Preparation of 2-(4-methoxyphenylthio)-3-methylthiophene

To a stirred solution of 2-bromo-3-methylthiophene (23.0 g, 0.13 mol) in anhydrous ether (100 ml) cooled to −78° C. was added 1.6M n-butyl lithium in hexane (81.3 ml, 0.13 mol) dropwise over 1 hour. The solution was stirred at −78° C. for an additional ¾ hour and a solution of 4-methoxyphenyl disulfide (38.14 g, 0.137 mol) in anhydrous ether (100 ml) was added rapidly. The temperature rose to 40° C. and then quickly dropped to −78° C. The mixture was stirred overnight as the temperature rose from −78° C. to ambient temperature. The suspension was cooled to −10° C. and 100 ml of water was added. The ether layer was separated and was washed with 0.5N KOH and with water, dried, filtered and concentrated in vacuo. The crude liquid residue was chromatographed on silica gel using 10% ethyl acetate hexane. This procedure gave 24.39 g of yellow liquid. N.M.R. supported the structure. Yield was 79%.

Step B: Preparation of 5-(4-methoxyphenylthio)-4-methylthiophene-2-sulfonamide To a stirred solution of 2-(4-methoxyphenylthio)-3-methylthiophene (24.35 g, 0.103 mol) in THF (100 ml) cooled to −75° C. was added 1.6M n-butyl lithium in hexane (67.5 ml, 0.108 mol) dropwise over ¾ hour. The solution was stirred for an additional 1 hour at −75° C. Then anhydrous sulfur dioxide was bubbled over the surface of the solution for 1¼ hour as the temperature was allowed to slowly rise from −75° to 10° C. Concentration of this solution in vacuo gave the lithio salt as a tan solid foam in quantitative yield. The solid was dissolved in saturated NaHCO$_3$ (150 ml) and N-chlorosuccinimide (20.0 g, 0.15 mol) was added over 15 minutes at ice bath temperature. The mixture was stirred at ice bath temperature for 1¼ hours, and then was extracted with chloroform. The chloroform solution was washed with water, dried, filtered and concentrated in vacuo. The sulfonyl chloride was obtained as a gray solid (39.5 g). The crude solid was dissolved in acetone (50 ml) and was added dropwise over ½ hour to concentrated NH$_4$OH (150 ml) at ice bath temperature. The mixture was stirred at ice bath temperature for 1½ hours and then was concentrated in vacuo to remove the acetone. The oil which separated was extracted into ether, washed with water, saturated NaHCO$_3$ and again with water. The dried ether solution was filtered and concentrated in vacuo. This procedure gave white solid (24.9 g). Yield was 77%. A sample was recrystallized from n-butyl chloride, m.p. 107°-109.5° C. Purity and structure were confirmed by C, H, N analyses, HPLC and NMR.

Step C: Preparation of 5-(4-Methoxyphenylsulfonyl)-4-methylthiophene-2-sulfonamide 5-(4-Methoxyphenylthio)-4-methylthiophene-2-sulfonamide (3.15 g, 0.01 mol) was dissolved in warm ethanol (20 ml) and water (20 ml) was added, followed by Oxone® (12.30, 0.02 mol). The suspension which formed was stirred at room temperature for 3½ hours. The acidic suspension was neutralized with excess NaHCO$_3$ and the mixture was concentrated in vacuo. The moist solid residue was taken up in ethyl acetate and water. The ethyl acetate solution was washed with saturated NaCl, filtered and concentrated in vacuo. This procedure gave a gum which crystallized from 1,2-dichloroethane as a white solid (3.16 g). Yield was 91%, m.p. 140.5°–143° C. Purity and structure were confirmed by C, H, N analyses, HPLC and NMR.

Step D: Preparation of 5-(4-Hydroxyphenylsulfonyl)-4-methylthiophene-2-sulfonamide 5-(4-methoxyphenylsulfonyl)-4-methylthiophene-2-sulfonamide (9.75 g, 0.028 mol) was suspended in methylene chloride (150 ml) and a 1.0M solution of boron tribromide in methylene chloride (90 ml, 0.09 mol) was added dropwise over ½ hour, at 0° C. Then the solution was stirred at ambient temperature for 5 hours. The solution was added to ice and water (500 ml) and ethyl acetate (500 ml) was added. The organic layer was separated, washed with saturated NaCl, saturated NaHCO$_3$ and again with saturated NaCl, dried, filtered and concentrated in vacuo. A yellow oil was obtained which crystallized from ethyl acetate-n-butyl chloride. Yield was 67%. The recrystallized white solid melted at 170°–172° C. Purity and structure were confirmed by C, H, N, analyses, HPLC and NMR.

Step E: Preparation of 5-(3-Dimethylaminomethylhydroxyphenylsulfonyl)-4-methylthiophene-2-sulfonamide To 5-(4-hydroxyphenylsulfonyl)-4-methylthiophene-2-sulfonamide (2.0 g, 0.006 mol) in ethanol (10 ml) was added 40% aqueous dimethylamine (2.7 g, 0.024 mol) followed by 37% aqueous formaldehyde (0.59, 0.0072 mol). The solution was stirred in an oil bath (98° C.) for 16½ hours. The solvent was removed in vacuo. The residual oil was taken up in ethyl acetate and extracted with dilute HCl. The HCl extract was basified with NaHCO$_3$ and the product was extracted into ethyl acetate. The extract was washed with water, dried, filtered and concentrated in vacuo. This procedure gave a solid foam in 44% yield which was converted to the hydrochloride salt with ethanolic HCl. The white solid HCl salt melted at 262°–263° C. Purity and structure were confirmed by C, H, N analyses, HPLC and NMR.

EXAMPLE 9

4-[(4-Isobutylaminomethyl)phenylsulfonyl]thiophene-2-sulfonamide

Step A: Preparation of 4-(4-bromomethylphenylsulfonyl)thiophene-2-sulfonyl chloride A solution of 18.0 g (0.053M) of 4-(4-methylphenylsulfonyl)-thiophene-2-sulfonyl chloride, 46.0 g (0.258 m) N-bromosuccinimide and 100 mg benzoyl peroxide in 175 ml CHCl$_3$ was heated at reflux and irradiated with a sun lamp for 45 minutes. The cooled mixture was then extracted with 3×100 ml portions of water, 5% sodium thiosulfate, brine and dried. The solvent was stripped to give the title compound as an oil.

Step B: Preparation of 4-(4-Bromomethylphenylsulfonyl)thiophene-2-sulfonamide To 22.0 g (0.053 mole) of product from Step A dissolved in 150 ml CHCl$_3$ was added gaseous NH$_3$ at 0°–10° C. for 5 minutes. The reaction mixture was then stirred at room temperature for 2.5 hours. The solvent was then removed in vacuo and the residue was purified by flash chromatography on silica gel eluting with 4% methanol/CHCl$_3$ to give pure title compound, as an oil.

Step C: Preparation of 4-[(4-Isobutylaminomethyl)phenylsulfonyl]thiophene-2-sulfonamide hydrochloride To 1.0 g (0.0025 ml) of product from Step B dissolved in 15 ml THF was added 5 ml isobutylamine and the resulting solution was stirred at room temperature for 48 hours. The solvent and excess amine were removed in vacuo and the residue was taken up in H$_2$O, acidified with 6N HCl and extracted with ethyl acetate. The aqueous phase was basified with concentrated NH$_4$OH to pH 8 and this was extracted with ethyl acetate. The organic phase was dried and the solvent evaporated to give a residue that was purified by flash chromatography on silica gel, eluting with 10% methanol/chloroform. Solvent removal from the homogeneous fractions gave an oil which was treated with ethanolic HCl with stirring for 1 hour. The resulting solid was collected and dried to provide pure title compound; m.p. 207°–209° C.

Following the procedures substantially as described in Example 9, but substituting for the isobutylamine used in Step C thereof, approximately equimolar amounts of morpholine, N-methylpiperazine, n-butylamine and α-picolinamine, there were produced respectively:

4-[4-(4-morpholinyl methyl)phenylsulfonyl]-2-thiophenesulfonamide hydrochloride, m.p. 238°–241° C. (dec.).

4-[4-[(4-Methyl-1-piperazinyl)methyl]phenylsulfonyl]-2-thiophenesulfonamide dihydrochloride, m.p. 238°–242° C. (dec.).

4-[4-(n-butylaminomethylphenylsulfonyl]-2-thiophenesulfonamide, m.p. 207°–209° C.

4-[4-(2-pyridinylmethylaminomethyl)phenylsulfonyl]-2-thiophenesulfonamide dihydrochloride, m.p. 90°–100° C.

EXAMPLE 10

4-(1-Ethylaminoethyl)-5-(4-hydroxyphenysulfonyl)thiophene-2-sulfonamide

Step A: Preparation of 3-Bromo-2-(4-methoxyphenylthio)thiophene

To a solution of 2,3-dibromothiophene (18.1 g, 0.075 mol) in anhydrous ether (100 ml) was added dropwise over ¾ hour 1.55M n-butyllithium in hexane (51 ml, 0.079 mol) at −70° C. under nitrogen atmosphere. The solution was stirred for an additional ¼ hour and then solid 4-methoxyphenyl disulfide (20.9 g, 0.075 mol) was added. The mixture was stirred over night as the temperature slowly rose to ambient conditions. The tan suspension which had formed was cooled to 0° C. and water (100 ml) was added carefully. The ether layer was separated and was washed with 10% NaOH and water until the wash was neutral. After the solution was dried over Na$_2$SO$_4$ it was filtered and concentrated in vacuo. The crude liquid obtained was twice distilled. This procedure gave 12.9 g of a colorless oil, bp 153°–157° C. at 0.5 mm. Yield was 57%. NMR supported the structure.

Step B: Preparation of
2-(4-Methoxyphenylthio)thiophene-3-carboxaldehyde

To a stirred solution of 3-bromo-2-(4-methoxyphenylthio)thiophene (12.77 g, 0.042 mol) in anhydrous ether (100 ml) cooled to −78° C. was added dropwise over 1 hour, 1.55M n-butyl lithium in hexane (28.7 ml, 0.045 mol) under nitrogen atmosphere. The solution was stirred at −78° C. for another hour and then the temperature was allowed to rise to −30° C. over ¼ hour. The temperature was lowered to −60° C. and dry dimethylformamide (6.2 g, 0.085 mol) was added over 5 minutes. The cooling bath was removed and the temperature was allowed to rise to 15° C. over ¾ hour. The mixture was cooled to −20° C. and acidified by slowly adding 3NHCl (40 ml). The ether layer was separated and washed with saturated NaCl, saturated NaHCO$_3$ and again with saturated NaCl. The solution was dried, filtered and concentrated in vacuo. A quantitative recovery of an amber oil which solidified to a waxy yellow solid was obtained. The product recrystallized from n-butyl chloride-hexane, mp 58°–60° C. The structure and purity were confirmed by NMR, mass spectral analysis and elemental analyses.

Step C: Preparation of
3-(1-Hydroxyethyl)-2-(4-methoxyphenylthio)thiophene

To a stirred solution of methylmagnesium bromide (20.7 ml, 0.06 mol of 2.9M solution in ether) in anhydrous ether (50 ml) cooled to −5° C. was added 2-(4-methoxyphenylthio)thiophene 3-carboxaldehyde (10.0 g, 0.04 mol) in anhydrous ether (40 ml) over a ½ hour period under nitrogen atmosphere. The mixture was stirred at 0° C. for 2 hours and was decomposed by adding a solution of NH$_4$Cl (5.3 g, 0.1 mol) in water (50 ml) over a 20 minute period at 0° to 15° C. The ether layer was separated, washed with 3NHCl, saturated, NaHCO$_3$ and water. It was dried, filtered and concentrated in vacuo at room temperature to obtain an amber oil. The product was purified by silica gel column chromatography using 50/50 hexane-ethyl acetate. This procedure gave 8.8 g of amber oil. Yield was 83%.

Step D: Preparation of
4-(1-Hydroxyethyl)-5-(4-methoxyphenylthio)thiophene-2-sulfonamide n-Butyllithium (42.2 ml, 0.0654 mol of a 1.55M solution in hexane) was added dropwise over 1 hour at −70° C. to a stirred solution of 3-(1-hydroxyethyl)-2-(4-methoxyphenylthio)thiophene in dry tetrahydrofuran (150 ml) under nitrogen atmosphere. The orange solution was stirred at −20° C. for about 2 hours. Then it was cooled to −50° C. and a solution of SO$_2$ (2.09 g, 0.0327 mol) in cold THF (20 ml) was added dropwise and the amber suspension was concentrated in vacuo. The tan gum remaining was taken up in water (100 ml) and sodium acetate (8.0 g, 0.098 mol) was added. To the resulting suspension was added hydroxylamine-O-sulfonic acid (5.64 g, 0.049 mol) and the mixture was stirred at ambient temperature over night. The reaction mixture was extracted with ethyl acetate (150 ml) and then the ethyl acetate solution was washed with water and concentrated in vacuo to obtain 11.5 g of amber oil. This material was purified by chromatography on silica gel using 40/60 ethyl acetate-hexane to give 5.4 g of white solid (48%). The product recrystallized from nitromethane, mp 149°–151° C. HPLC, elemental analyses and NMR supported the purity and structure.

Step E: Preparation of
4-(1-Hydroxyethyl)-5-(4-methoxyphenylsulfonyl)thiophene-2-sulfonamide 4-(1-Hydroxyethyl)-5-(4-methoxyphenylthio)thiophene-2-sulfonamide (1.39 g, 0.004 mol) was dissolved in ethanol (5 ml) and water (5 ml) was added. To this cloudy solution was added Oxone ® (3.69 g, 0.006 mol) and the mixture was stirred at room temperature for 6 hours. Solid NaHCO$_3$ was added to neutralize the mixture and the suspension was filtered. The solids were washed with ethanol and the filtrate and washings were combined and concentrated in vacuo. The residual solids were taken up in ethyl acetate (50 ml) and water (50 ml). The ethyl acetate layer was dried, filtered and concentrated in vacuo to obtain 1.51 g of solid. The product was purified by recrystallization from nitromethane to give 0.86 g of white solid, m.p. 141°–144° C. (57%). Purity and structure were confirmed by HPLC, C, H, N analyses and NMR.

Step F: Preparation of
4-(1-Acetamidoethyl)-5-(4-methoxyphenylsulfonyl)thiophene-2-sulfonamide Acetonitrile (30 ml) was cooled in ice and concentrated H$_2$SO$_4$ (4.4 ml, 0.083 mol) was added over about 5 minutes. Then 4-(1-hydroxyethyl)-5-(4-methoxyphenylsulfonyl)thiophene-2-sulfonamide (3.13 g, 0.0083 mol) in acetonitrile (20 ml) was added and the solution was stirred at room temperature over the week-end. The reaction was diluted with water (10 ml) and was neutralized with NaHCO$_3$. The suspension was filtered and the solids were washed with acetonitrile. The filtrate and washings were concentrated in vacuo. The residual oil was taken up in ethyl acetate and water. The ethyl acetate was separated, washed with saturated NaCl, dried, filtered and concentrated in vacuo. A white solid foam was obtained, 3.18 g, yield 92%. The structure was supported by NMR analyses.

Step G: Preparation of
4-(1-Ethylaminoethyl)-5-(4-methoxyphenylsulfonyl)thiophene-2-sulfonamide To a refluxing solution of 4-(1-acetamidoethyl)-5-(4-methoxyphenyl)thiophene-2-sulfonamide (3.1 g, 0.0074 mol) in dry tetrahydrofuran (50 ml) was added 10M dimethylsulfide borane complex (3.0 ml, 0.03 mol) in tetrahydrofuran (10 ml) dropwise over ½ hour under nitrogen atmosphere. The solution was refluxed for 2½ hours. The reaction was cooled in ice and acidified with 6NHCl (4 ml) added dropwise. The acidified mixture was concentrated in vacuo. The residual white solid was taken up in water and ethyl acetate, the ethyl acetate was washed with saturated NaCl, dried, filtered and concentrated in vacuo to give 2.7 g of solid foam which was purified by chromatography on silica gel using 7% methanol in chloroform. The pure oil recovered (1.58 g) was converted to the hydrochloride salt with ethanolic HCl. The white solid decomposed slowly at temperature above 140° C. Purity and structure of the product were confirmed by elemental analyses, HPLC and NMR. The yield was 53%.

Step H: Preparation of 4-(1-Ethylaminoethyl)-5-(4-hydroxyphenylsulfonyl)thiophene-2-sulfonamide To 60% NaH suspended in mineral oil (810 mg, 20.4 mmol) in dry DMF (30 ml) was added ethanethiol (1.37 ml, 18.5 mmol) at ice bath temperature under nitrogen. The mixture was stirred for ¼ hour and then treated with 4-(1-ethylaminoethyl)-5-(4-methoxyphenylsulfonyl)thiophene-2-sulfonamide (750 mg, 1.85 mmol). The reaction was stirred in an oil bath (100° C.) for 1¾ hours. The resulting solution was cooled in ice and was acidified with 6NHCl (5 ml). The acidified solution was washed with ether and was basified with NaHCO$_3$. The product was extracted into ethyl acetate, washed with saturated NaCl, dried, filtered and concentrated in vacuo to give a white solid (540 mg). The yield was 75%. The product was converted to the hydrochloride salt with ethanolic HCl. The white solid obtained decomposed slowly >180° C. Purity and structure were confirmed by C, H, N analyses, HPLC and NMR.

EXAMPLE 11

4-(1-Hydroxyethyl)-5-[(3-dimethylaminomethyl-4-hydroxyphenyl)sulfonyl]thiophene-2-sulfonamide Step A: Preparation of 4-(1-hydroxyethyl)-5-(4-hydroxyphenylsulfonyl)thiophene-2-sulfonamide Ethanethiol (2.1 ml, 0.028 mol) was added dropwise over a 10 minute period to a stirred suspension of 60% NaH in mineral oil (1.4 g, 0.035 mol) in dimethylformamide (50 ml) at ice bath temperature under a nitrogen atmosphere. After the sodium hydride had reacted, 4-(1-hydroxyethyl-5-(4-methoxyphenylsulfonyl)thiophene-2-sulfonamide (2.64 g, 0.007 mol) was added to the solution and the solution was heated in an oil bath at 80° C. for 3½ hours. The solution was cooled to ice bath temperature and 3N HCl was added (20 ml). The acidic mixture was extracted with ethyl acetate. The ethyl acetate extract was washed with saturated NaCl, saturated NaHCO$_3$ and again with saturated NaCl, dried, filtered and concentrated in vacuo. The crude amber oil obtained was washed with pet. ether several times to remove mineral oil and was solidified by triturating in nitromethane. A white solid was obtained, 2.2 g. Recrystallization from nitromethane gave material of mp 173°-175° C. Yield 87%. Purity and structure were confirmed by HPLC, C, H, N analyses and NMR.

Step B: Preparation 4-(1-hydroxyethyl)-5-[(3-dimethylaminomethyl-4-hydroxyphenyl)sulfonyl]thiophene-2-sulfonamide Employing the procedure substantially as described in Example 8, Step E but starting with the product from Step A of this Example 11 the title compound is produced.

EXAMPLE 12

4-(1-Hydroxyethyl)-5-[(3-dimethylaminomethyl-4-hydroxyphenylthio)thiophene-2-sulfonamide Step A: Preparation of 4-(1-Hydroxyethyl)-5-(4-hydroxyphenylthio)thiophene-2-sulfonamide Ethanethiol (2.1 ml, 0.028 mol) was added dropwise over 10 minutes to a stirred suspension of 60% NaH in mineral oil (1.28 g, 0.032 mol) in DMF (30 ml) at ice bath temperature under nitrogen. After the sodium hydride had reacted, 4-(1-hydroxyethyl)-5-(4-methoxyphenylthio)thiophene-2-sulfonamide (1.0 g, 0.0029 mol) was added and the solution was stirred at steam bath temperature over night. The mixture was cooled in ice and acidified with 3N HCl (20 ml). The mixture was extracted with ethyl acetate and the extract was washed with saturated NaCl, saturated NaHCO$_3$ and again with saturated NaCl. The extract was dried, filtered and concentrated in vacuo. The residual oil was washed with pet ether to remove the mineral oil and was purified by silica gel chromatography using 10% methanol in chloroform. The white solid product was obtained in 61% yield, mp. 133°-137° C. Purity and structure were confirmed by HPLC, C, H, N analysis and NMR.

Step B: Preparation 4-(1-hydroxyethyl)-5-[(3-dimethylaminomethyl-4-hydroxyphenyl)thio]thiophene-2-sulfonamide Employing the procedure substantially as described in Example 8, Step E but starting with the product from Step A of this Example 12, the title compound is produced.

EXAMPLE 13

5-(3-Ethylamino-3-phenyl-1-propylsulfonyl)thiophene-2-sulfonamide

Step A: Preparation of 2-(3-Hydroxypropylthio)thiophene

To a suspension of lithium aluminum hydride (20.1 g, 0.53 mol) in THF (125 ml), cooled to 0° C. was added a solution of 5-(2-carboxyethylthio)thiophene (25.0 g, 0.13 mol) in THF (125 ml) dropwise. The mixture was refluxed for 2 hours, cooled to 0° C. and saturated Na$_2$SO$_4$ was added dropwise. The solid was filtered, washed with CHCl$_3$ and the filtrate was concentrated. Water was added to the residue and extracted with CHCl$_3$. Drying and solvent evaporation gave an oily, product (21.7 g, 96%).

Step B: Preparation of 3-(2-Thienylthio)acetaldehyde

To a solution of oxalyl chloride (1.6 ml, 18.9 mmol) in CH$_2$Cl$_2$ (47.2 ml), cooled to −60° C. was added a solution of DMSO (2.7 ml, 37.8 mmol) in CH$_2$Cl$_2$ (8.6 ml) dropwise. A solution of the product from Step A (3.0 g, 17.2 mmol) in CH$_2$Cl$_2$ (17.2 ml) was added dropwise and the mixture was stirred at −60° C. for 0.5 hour. Triethylamine (12.0 ml, 86 mmol) was added and the mixture was stirred at room temperature for 1 hour. Water was added, separated from the organic layer and extracted with CH$_2$Cl$_2$. The combined organic layers were washed with 1N HCl, dilute Na$_2$CO$_3$ solution, water and brine. Drying and solvent evaporation gave an oily product (2.9 g).

Step C: Preparation of 2-(3-Hydroxy-3-phenylpropylthio)thiophene

To phenylmagnesium bromide (47.0 ml, 3.0M in ether, 0.14 mol), cooled to 0° C. was added a solution of product from Step B (17.2 g, 0.10 mol) in THF (167 ml) dropwise, maintaining a temperature of 10° C. The reaction mixture was stirred at room temperature overnight. Saturated NH$_4$Cl solution was added dropwise, the mixture filtered through super-cel and the solid washed with CHCl$_3$. The filtrate was concentrated, water added and extracted with CHCl₃. Drying and solvent evaporation gave an oil (25.0 g) and column chromatography (silica gel, 100% CHCl₃) gave the title compound (18.9 g, 76%).

Similarly prepared was 2-[3-hydroxy-3-(4-methoxyphenyl)propylthio]thiophene, an oil (60% yield).

Step D: Preparation of 2-(3-Methoxyethoxymethoxy-3-phenylthio)thiophene

To a solution of product from Step C (3.0 g, 12.0 mmol) and N,N-diisopropylethylamine (3.1 ml, 18.0 mmol) in CH₂Cl₂ (24 ml) was added methoxyethoxymethyl chloride (2.0 ml, 18.0 mmol) dropwise. The solution was stirred at room temperature overnight. The reaction mixture was washed with cold 0.5NHCl, saturated NaHCO₃ solution, water and brine. Drying and solvent evaporation gave an oil (3.6 g) and column chromatography (silica gel, 10% ethyl acetate hexane) gave the title compound (2.9 g, 71%).

Step E: Preparation of 5-(3-Methoxyethoxymethoxy-3-phenylthio)thiophene-2-sulfonamide To a solution of product from Step D (4.9 g, 14.5 mmol) in THF (72.5 ml), cooled to −23° C. was added n-butyllithium (10.9 ml, 1.6M in ether-hexane, 17.4 mmol) dropwise. The mixture was stirred at −23° C. for 0.5 hour. Sulfur dioxide was bubbled vigorously over the reaction surface, maintaining cooling for 40 minutes, producing a color change from brown to yellow. Ether was added and the solution was stirred at room temperature for 2 hours. The solvent was evaporated, the residue dissolved in CH₂Cl₂ (181 ml) and cooled at 0° C. N-chlorosuccinimide (1.9 g, 14.5 mmol) was added and the solution was stirred at room temperature overnight. Filter-aid was added, the mixture was filtered and the solvent evaporated. The residue was dissolved in acetone and poured into NH₄OH (75 ml). The solution was concentrated, water added, and the mixture was extracted with ethyl acetate. The organic layers were washed with brine, dried and concentrated to give an oily, product (5.0 g).

Step F: Preparation of 5-(3-Methoxyethoxymethoxy-3-phenylpropylsulfonyl)-thiophene-2-sulfonamide To a solution of the product from Step E (5.0 g, 11.9 mmol) in methanol (24 ml) was added dropwise a solution of OXONE ® (12.4 g, 20.2 mmol) in water (67 ml) and the resulting suspension was stirred at room temperature overnight. The mixture was concentrated, water added, and the mixture was extracted with ethyl acetate. The organic layers were washed with brine, dried and concentrated to give an oil (4.9 g) and column chromatography (silica gel, 40–45% ethyl acetate-hexane) gave the title compound 3.8 g, 70%).

Step G: Preparation of 5-(3-Hydroxy-3-phenylpropylsulfonyl)thiophene-2-sulfonamide To a solution of sulfuric acid (76.7 ml) in water (76.7 ml), cooled to 0° C. was added a solution of compound from Step F (5.2 g, 11.5 mmol) in methanol (76.7 ml) and the reaction mixture was stirred at room temperature for 1 hour. Water was added, extracted with ethyl acetate and the organic layers were washed with saturated NaaHCO₃ solution and brine. Drying and solvent evaporation gave an oil (4.4 g) and column chromatography (silica gel, 40% ethyl acetate-hexane) gave a solid product (2.3 g, 56%); m.p. 119°–121° C.

Step H: Preparation of 5-(3-Acetamido-3-phenylpropylsulfonyl)thiophene-2-sulfonamide To sulfuric acid (3.4 ml), cooled at 0° C. was added a solution of compound from Step G (1.2 g, 3.3 mmol) in acetonitrile (11 ml) dropwise and the solution was stirred at room temperature overnight. The mixture was poured into ice (75 ml) and stirred for 1 hour. The solution was extracted with ethyl acetate and the organic layers were washed with saturated NaHCO₃ solution and brine. Drying and solvent evaporation gave a solid product (1.3 g).

Step I: Preparation of 5-(3-Ethylamino-3-phenylpropylsulfonyl)thiopene-2-sulfonamide hydrogen maleate To a solution of compound from Step H (1.3 g, 3.2 mmol) in THF (18.8 ml), heated to reflux temperature was added borane-methyl sulfide complex (0.96 ml, 10.0M in BH₃, 9.6 mmol) dropwise. The reaction mixture was refluxed for 1 hour, collecting the methyl sulfide via a short path distillation apparatus. The solution was concentrated, the residue dissolved in isopropanol and salt formation was afforded with maleic acid to yield the title compound (1.2 g, 75%); m.p. 179°–181° C.

EXAMPLE 14

5-[3-Ethylamino-3-(4-hydroxyphenyl)propylsulfonyl]-thiophene-2-sulfonamide hydrogen maleate

Step A: Preparation of 5-[3-hydroxy-3-(4-methoxyphenyl)propylthio]thiophene-2-sulfonamide To a solution of 2-[3-hydroxy-3-(4-methoxyphenyl)-propylthio]thiophene (3.3 g, 0.012 mol) in THF (60 ml), cooled to −23° C. was added n-butyllithium (15.0 ml, 1.6M in ether-hexane, 0.024 mol) dropwise. The mixture was stirred at −23° C. for 2 hours. The reaction was cooled to −78° C. and liquid SO₂ (0.5 ml, 0.012 mol) was added. After stirring at room temperature for 1.5 hour, acetic acid (0.7 ml) and hexane (60 ml) were added. The reaction mixture was filtered and the solid washed with hexane. The solid was dissolved in water (20 ml) and sodium acetate (1.6 g, 0.012 mol) and hydroxylamine —O— sulfonic acid (1.6 g, 0.014 mol) were added. The mixture was then stirred at room temperature overnight. The aqueous phase was extracted with ethyl acetate and the combined organic layers were dried. Solvent evaporation gave an oil (2.4 g); column chromatography (silica gel, 40% ethyl acetate-hexane) and recrystallization from CHCl₃ gave the title compound (1.2 g, 28%); m.p. 111°–112° C.

Anal. Calc'd. for C₁₄H₁₇NO₄S₃: C, 46.77; H, 4.78; N, 3.90. Found: C, 46.81; H, 4.78; N, 4.24.

Step B: Preparation of 5-[3-Hydroxy-3-(4-methoxyphenyl)propylsulfonyl]thiophene-2-sulfonamide Methanol (n 10 ml) was added to the compound from Step A (1.0 g, 2.8 mmol) to produce a solution. Sodium tungstate (Na₂WO₄.2H₂O, 0.03 g, 0.084 mmol) was added, followed by H₂O₂ (0.7 ml, 30% in water, 5.6 mmol) dropwise and the resulting mixture was stirred at room temperature overnight. Sodium sulfite (10% solution) was added to destroy peroxides and the reaction mixture was concentrated. Water was added and extracted with ethyl acetate. Drying and solvent evaporation gave a solid; recrystallization from CHCl$_3$ gave the title compound (0.8 g, 42%); m.p. 129°–130° C.

Anal. Calc'd. for C$_{14}$H$_{17}$NO$_6$S$_3$: C, 42.95; H, 4.38; N, 3.58. Found: C, 43.25; H, 4.39; N, 3.64.

Step C: Preparation of 5-[3-Acetamido-3-(4-methoxyphenyl)propylsulfonyl]-thiophene-2-sulfonamide To sulfuric acid (5.2 ml), cooled to 0° C. was added a solution of product from Step B (2.0 g, 5.1 mmol) in acetonitrile (17 ml) dropwise and the solution was stirred at room temperature overnight. The mixture was poured into ice (100 ml) and stirred for 1 hour. The solution was extracted with ethyl acetate and the organic layers were washed with water and saturated NaHCO$_2$ solution. Drying and solvent evaporation gave the title compound (2.0 g, 91%).

Step D: Preparation of 5-[3-ethylamino-3-(4-methoxyphenyl)propylsulfonyl]-thiophene-2-sulfonamide hydrogen maleate To a solution of product from Step C (2.0 g, 4.6 mmol) in THF (23 ml), heated to reflux temperature was added borane methyl sulfide complex (1.4 ml, 10.0M in BH$_3$, 13.8 mmol) dropwise. The reaction mixture was refluxed for 1 hour, collecting the methyl sulfide via a short path distillation apparatus. The solution was concentrated to dryness, 6N HCl (50 ml) added, and the mixture refluxed for 1 hour. The reaction mixture was concentrated and the residue dissolved in ethyl acetate. Saturated NaHCO$_3$ solution was added, separated from the organic layer and extracted with ethyl acetate. Drying and solvent evaporation gave an oil (1.9 g); salt formation was afforded with maleic acid in isopropanol-ether-chloroform to yield the title compound (0.7 g, 29%); m.p. 110°–120° C.

Anal. Calc'd. for C$_{20}$H$_{26}$N$_2$O$_9$S$_3$: C, 44.92; H, 4.91; N, 5.24. Found: C, 44.76; H, 4.55; N, 5.14.

Step E: Preparation of 5-[3-ethylamino-3-(4-hydroxyphenyl)propylsulfonyl]-thiophene-2-sulfonamide hydrogen maleate To a solution of product from Step D, (0.7 g, 1.6 mmol) in CH$_2$Cl$_2$ (27 ml) cooled to −78° C. was added BBr$_3$ (5.3 ml, 1.0M in CH$_2$Cl$_2$, 5.3 mmol) dropwise and the solution was stirred at room temperature overnight. The mixture was cooled to 0° C., water and saturated NaHCO$_3$ solution were added and the mixture was extracted with ethyl acetate. Drying and solvent evaporation gave an oil (0.7 g). Salt formation was afforded with maleic acid in CHCl$_3$ to yield the title compound (0.4 g, 57%); m.p. 152°–154° C.

Anal. Calc'd. for C$_{19}$H$_{24}$N$_2$O$_9$S$_3$: C, 43.83; H, 4.66; N, 5.38. Found: C, 43.78; H, 4.84; N, 5.61.

EXAMPLE 15

4-(2-Dimethylaminomethyl-4-methoxyphenylsulfonyl)-thiophene-2-sulfonamide

To 0.96 g (3 mmol) 4-(4-methoxyphenylsulfonyl)thiophene-2-sulfonamide dissolved in 10 ml THF and cooled to −78° C. under N$_2$ was added 18 mmole n-butyllithium (in hexane) dropwise at −70° C. and the resulting solution was stirred at −78° for 15 minutes. Then, 1.39 g (7.5 mmole) N,N-dimethyl-N-methylene imminium iodide was added portionwise and the resulting reaction mixture was stirred at −70° C. for 3 hours. The reaction was quenched with 25 ml saturated ammonium chloride solution and extracted with 4×75 ml portions of ethyl acetate. The combined organic extracts were dried and evaporated to give an oil that was purified by flash chromatography on silica gel eluting with CHCl$_3$ (9)/MeOH (1) to give the desired product (free base) as a clean oil. Treatment with ethanolic HCl provided the hydrochloride salt, m.p. 260°–263° (dec).

EXAMPLE 16

5-(3-Isobutylaminomethyl-4-hydroxyphenylsulfonyl)-thiophene-2-sulfonamide

Step A: Preparation of [2-Hydroxy-5-(5-sulfonamidothien-2-ylsulfonyl)-phenyl]methyl trimethylammonium iodide A mixture of 5-(3-dimethylaminomethyl-4-hydroxyphenylsulfonylthiophene-2-sulfonamide (2.5 g, 6.6 mm) and methyl iodide (1.9 g, 13.2 mm) in ethanol (30 ml) was refluxed eighteen hours. The reaction was cooled in ice and filtered. The solid was recrystallized from a mixture of ethanol/methanol; m.p. 138°–140° C.

Step B: Preparation of 5-(3-Isobutylaminomethyl-4-hydroxyphenylsulfonyl)-thiophene-2-sulfonamide The tetramethyl iodide salt (1 g, 1.9 mm) and 35 ml isobutylamine were heated at 65° C. for two hours. The reaction was filtered hot and the filtrate concentrated in vacuo. The resulting oil was triturated with chloroform to form a solid (430 mg). The solid was recrystallized from ethanol. The product was converted to its hydrochloride salt by treatment with ethanolic hydrogen chloride (389 mg) m.p. 214°–215° C.

Employing the procedure substantially as described in Example 14, but substituting for the isobutylamine used therein, ethylamine cyclopropylmethylamine, morpholine, 1-methylpiperazine, n-butylamine, 2-pyridinylmethylamine, and isobutylamine along with the appropriate thiophene derivative there were produced, respectively:

5-(3-ethylaminomethyl-4-hydroxyphenylsulfonyl)thiophene-2-sulfonamide, m.p. 241°–242° C.;

5-(3-cyclopropylaminomethyl-4-hydroxyphenylsulfonyl)thiophene-2-sulfonamide;

4-[4-(4-morpholinylmethyl)phenylsulfonyl]thiophene-2-sulfonamide hydrochloride, m.p. 238°–241° C. (dec.);

4-[4-[(4-Methyl-1-piperazinyl)methyl]phenylsulfonyl]-thiophene-2-sulfonamide dihydrochloride, m.p. 238°–242° C. (dec.);

4-[4-(n-butylaminomethyl)phenylsulfonyl]thiophene-2-sulfonamide, m.p. 207°–209° C.;

4-[4-(2-pyridinylmethylaminomethyl)phenylsulfonyl]-thiophene-2-sulfonamide dihydrochloride, m.p. 90°–100° C.; and 4-[4-(isobutylaminomethyl)phenylsulfonyl]thiophene-2-sulfonamide, hydrochloride, m.p. 208°–209° C.

EXAMPLE 17

5-[3-(3-dimethylaminomethyl-4-hydroxyphenyl)propyl-sulfonyl]thiophene-2-sulfonamide Step A: Preparation of 3-[2-(4-Methoxybenzoyl)ethylsulfonyl]thiophene-2-sulfonamide A solution of Jones Reagent was prepared by dissolving 26.72 g of chromic trioxide in 23 ml of concentrated sulfuric acid and diluting with water to a volume of 100 ml. To a solution of 5-[3-hydroxy-3-(4-methoxyphenyl)propylsulfonyl]thiophene-2-sulfonamide (1.4 g, 3.9 mmol) in acetone (39 ml) was added Jones Reagent (5.8 ml) dropwise and the reaction was stirred at room temperature for 1 hour. Water was added to the mixture and the mixture was extracted with ethyl acetate. Drying and solvent evaporation gave a solid (1.3 g.) Recrystallization from CHCl$_3$ gave the title compound (0.8 g, 53%).

Step B: Preparation of 5-[3-(4-methoxyphenyl)propylsulfonyl]thiophene-2-sulfonamide To a solution of product from Step A (0.4 g, 1.0 mmol) in trifluoracetic acid (1.5 ml) was added triethylsilane (0.6 ml, 4.0 mmol) and the reaction was refluxed for 3 hours. The mixture was made basic with saturated bicarbonate solution and extracted with ethyl acetate. Drying and solvent evaporation gave a solid (0.7 g). Recrystallization from CHCl$_3$ gave the title compound (270 mg, 68%); m.p. 136°–138° C.

Step C: Preparation of 5-[3-(4-hydroxyphenyl)propylsulfonyl]thiophene-2-sulfonamide To a suspension of product from Step B, (3.0 g, 8.0 mmol) in CH$_2$Cl$_2$ (132 ml), cooled to −78° C., was added boron tribromide (25.9 ml, 1.0M in CH$_2$Cl$_2$, 25.9 mmol) dropwise and the resulting mixture was stirred at room temperature overnight. The reaction was cooled to 0° C., water and saturated bicarbonate solution added and extracted with ethyl acetate. Drying and solvent evaporation gave a solid (2.9 g); recrystallization from CHCl$_3$ gave the title compound (1.5 g, 52%); m.p. 112°–115° C.

Step D: Preparation of 5-[3-(3-dimethylaminomethyl-4-hydroxyphenyl)propyl-sulfonyl]-thiophene-2-sulfonamide To a solution of product from Step C, (1.2 g, 3.3 mmol) in ethanol (16.5 ml) was added formaldehyde (0.3 ml, 37% in water, 3.6 mmol) and dimethylamine (0.8 ml, 40% in water, 6.6 mmol). The reaction was refluxed for 3 hours and then stirred at room temperature overnight. The solution was concentrated, 3N HCl added and extracted with ethyl acetate. The aqueous phase was made basic with saturated bicarbonate solution and extracted with ethyl acetate. Drying and solvent evaporation gave and oil (1.1 g). Column chromatography (silica gel, 5% methanol-CHCl$_3$) gave the title compound (0.8 g, 57%).

EXAMPLE 18

| Solution Composition | a | b |
| --- | --- | --- |
| Compound | 1 mg. | 15 mg. |
| Monobasic sodium phosphate.2H$_2$O | 9.38 mg. | 6.10 mg. |
| Dibasic sodium phosphate.12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound, phosphate buffer salts, and benzalkonium chloride are added to and admixed with water. The pH of the resulting admixture is adjusted to 6.8 and the final formulation diluted to volume. The formulation is rendered sterile by appropriate means, such as starting the preparative procedure with sterile components and proceeding under sterile conditions, irradiating or autoclaving the finished formulation, or the like.

EXAMPLE 19

Compound: 5 mg.
petrolatum q.s. ad.: 1 gram

Compound and the petrolatum are aseptically combined.

EXAMPLE 20

Compound: 1 mg.
Hydroxypropylcellulose q.s.: 12 mg.

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 21

Compound: 0.10%
Gelrite ®: 0.6%
benzalkonium chloride: 0.01%
mannitol: 4%
sufficient water to make: 100%

What is claimed is:

1. A compound of structural formula:

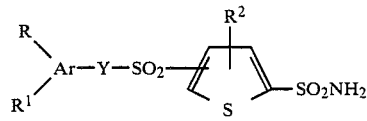

or an ophthalmologically acceptable salt thereof, wherein:

Ar is an aromatic moiety selected from benzene, thiophene and furan;

R is hydrogen, hydroxy, C$_{1-3}$alkoxy, C$_{1-3}$alkyl, or halo;

R$^1$ is hydrogen, halo or —X—NR$^3$R$^4$ wherein X is C$_{1-5}$ alkylene;

R$^3$ is hydrogen or C$_{1-5}$ alkyl; and

R$^4$ is (a) hydrogen (b) C$_{1-5}$alkyl, either unsubstituted or substituted with:

(i) hydroxy,
(ii) $C_{1-3}$alkoxycarbonyl,
(iii) carboxy,
(iv) $C_{3-6}$cycloalkyl;

$R^2$ is hydrogen or $C_{1-5}$alkyl, either straight or branched chain, either unsubstituted or substituted with —OH or —$NR^5R^6$ wherein $R^5$ and $R^6$ are independently selected from hydrogen, $C_{1-5}$alkyl either straight or branched chain; and Y is
(a) a bond,
(b) X, or
(c) X—$NR^5R^6$ with the proviso that at least one of $R^1$, $R^2$ or Y includes a basic substituent —$NR^3R^4$ or $NR^5R^6$; and that the 3-position of the thiophene is unsubstituted.

2. The compound of claim 1 wherein Ar is benzene.
3. The compound of claim 2 wherein $R^2$ is hydrogen or $C_{1-5}$ alkyl.
4. The compound of claim 3 of structural formula:

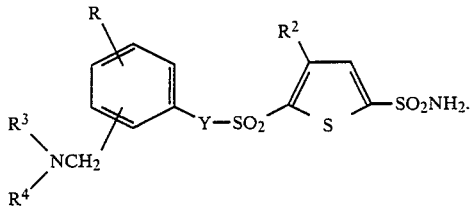

5. A compound of structural formula:

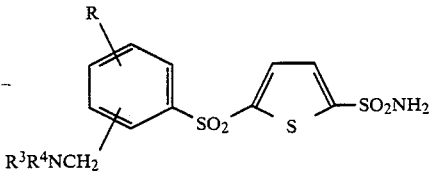

or an ophthalmologically acceptable salt thereof, wherein:
R is hydrogen, hydroxy, $C_{1-3}$ alkoxy, $C_{1-3}$ alkyl, or halo;
$R^3$ is hydrogen or $C_{1-5}$ alkyl; and $R^4$ is
(a) hydrogen
(b) $C_{1-5}$ alkyl, either unsubstituted or substituted with:
(i) hydroxy,
(ii) $C_{1-3}$ alkoxycarbonyl,
(iii) carboxy,
(iv) $C_{3-6}$ cycloalkyl.

6. The compound of claim 5 which is
5-(3-diethylaminomethyl-4-hydroxyphenylsulfonyl)thiophene-2-sulfonamide; or
5-[3-(2-methylpropyl)aminomethylphenylsulfonyl]thiophene-2-sulfonamide; or
5-[3-ethylamino-3-(4-hydroxyphenyl)propylsulfonyl]-thiophene-2-sulfonamide;
5-[3-(3-dimethylaminomethyl-4-hydroxyphenyl)propylsulfonyl]thiophene-2-sulfonamide;
5-(3-dimethylaminomethyl-4-hydroxyphenylsulfonyl)-thiophene-2-sulfonamide; or an ophthalmologically acceptable salt thereof.

7. The compound of claim 6 which is 5-(3-dimethylaminomethyl-4-hydroxyphenylsulfonyl)thiophene-2-sulfonamide or an ophthalmologically acceptable salt thereof.

8. An ophthalmic formulation for treating elevated intraocular pressure and/or glaucoma comprising an ophthalmogically acceptable carrier and an effective intraocular pressure lowering and/or antiglaucoma amount of the compound of claim 1.

9. A method of treating elevated intraocular pressure and/or glaucoma which comprises the topical ocular administration, to a patient in need of such treatment, of an effective intraocular pressure lowering and/or antiglaucoma amount of the compound of claim 1.

10. An ophthalmic formulation for treating elevated intraocular pressure and/or glaucoma comprising an ophthalmogically acceptable carrier and an effective intraocular pressure lowering and/or antiglaucoma amount of the compound of claim 5.

11. A method of treating elevated intraocular pressure and/or glaucoma which comprises the topical ocular administration, to a patient in need of such treatment, of an effective intraocular pressure lowering and/or antiglaucoma amount of the compound of claim 5.

* * * * *